United States Patent [19]

Prince

[11] Patent Number: 4,964,847
[45] Date of Patent: Oct. 23, 1990

[54] METHOD AND APPARATUS FOR ESTIMATING HEMATOCRIT IN A BLOOD CONSTITUENT PROCESSING SYSTEM

[75] Inventor: Paul R. Prince, Fountain Valley, Calif.

[73] Assignee: Baxter International Inc., Deerfield, Ill.

[21] Appl. No.: 289,424

[22] Filed: Dec. 23, 1988

Related U.S. Application Data

[63] Continuation of Ser. No. 920,341, Oct. 17, 1986, abandoned.

[51] Int. Cl.$^5$ .............................................. A61M 37/00
[52] U.S. Cl. .......................................... 604/4; 436/70
[58] Field of Search ................ 436/10.43, 63, 70, 148; 604/4-6

[56] References Cited

U.S. PATENT DOCUMENTS

| | | |
|---|---|---|
| 1,963,011 | 2/1928 | Albersheim et al. |
| 3,549,994 | 12/1970 | Rothermel et al. ................... 436/70 |
| 4,030,888 | 6/1977 | Yamamoto et al. .................. 436/70 |
| 4,340,565 | 7/1982 | Kitajima et al. ..................... 436/70 |
| 4,491,012 | 1/1985 | Peterson ............................... 436/63 |
| 4,650,458 | 3/1987 | Dahlberg et al. ...................... 604/5 |
| 4,680,025 | 7/1987 | Kruger et al. .......................... 604/4 |

FOREIGN PATENT DOCUMENTS

| | | |
|---|---|---|
| 9222041 | 12/1945 | France . |
| 1468325 | 2/1966 | France . |
| 0049265 | 3/1985 | Japan ..................................... 436/70 |

OTHER PUBLICATIONS

"Experimental Methods for Engrs." Holman, McGraw Hill, 2nd Edition, pp. 296, 297.
Laboratory Techniques Appendix—Chapter A31, "Serum Viscosity" by William J. Williams—p. 1660.
Clinical Manifestations of Erythrocyte Discorders—Chapter 8, p. 61 and Clinical Manifestations of Granulocyte and Monocyte Disorders—Chapter 9 by Marshall A. Litchman, pp. 62-33.
Swank, Roth and Jansen—Journal of Applied Physiology "Screen Filtration Pressure Method and Adhesiveness and Aggregation of Blood Cells," vol. 19, (1964), pp. 340-346.
From the Department of Surgery, Tulane University, New Orleans, Louisana "Screen Filtration Pressure and Quantity of Microaggregates: A Nonexisting Relationship" by B. Risberg, vol. 19, No. 6—pp. 749-753.
Microvascular Research 3,—"Hemolysis During Filtration Through Micropores: A Scanning Electron Microscopic and Hemorheologic Correlation" by Chien et al., College of Physicians and Surgeons, Columbia University, New York, N.Y.
Developments in Hematology and Immunology—"Red Cell Deformability and Filterability"—Proceedings of the Second Workshop Held in London, 23 and 24, Sep. 1982.

Primary Examiner—Robert A. Wax
Assistant Examiner—T. J. Wallen
Attorney, Agent, or Firm—Bradford R. L. Price; June M. Bostich

[57] ABSTRACT

During an initial priming procedure, the blood draw/return needle(s) fluid flow system is primed with a nonblood fluid (e.g. a saline solution) having known fluid viscosity. The pressure drop occurring across the needle orifice(s) is determined at a knonw flow rate for this predetermined fluid of known viscosity. During subsequent blood constitutent processing operations, the pressure drop across the needle orifice is measured for a second known flow rate of blood constituents. From these measured relative values of pressure and flow rates, the blood viscosity value can be calculated and used to estimate (e.g. via a table look-up or analytical calculation procedure) a hematocrit value of the blood constitutents as a function of the measured blood viscosity value.

8 Claims, 3 Drawing Sheets

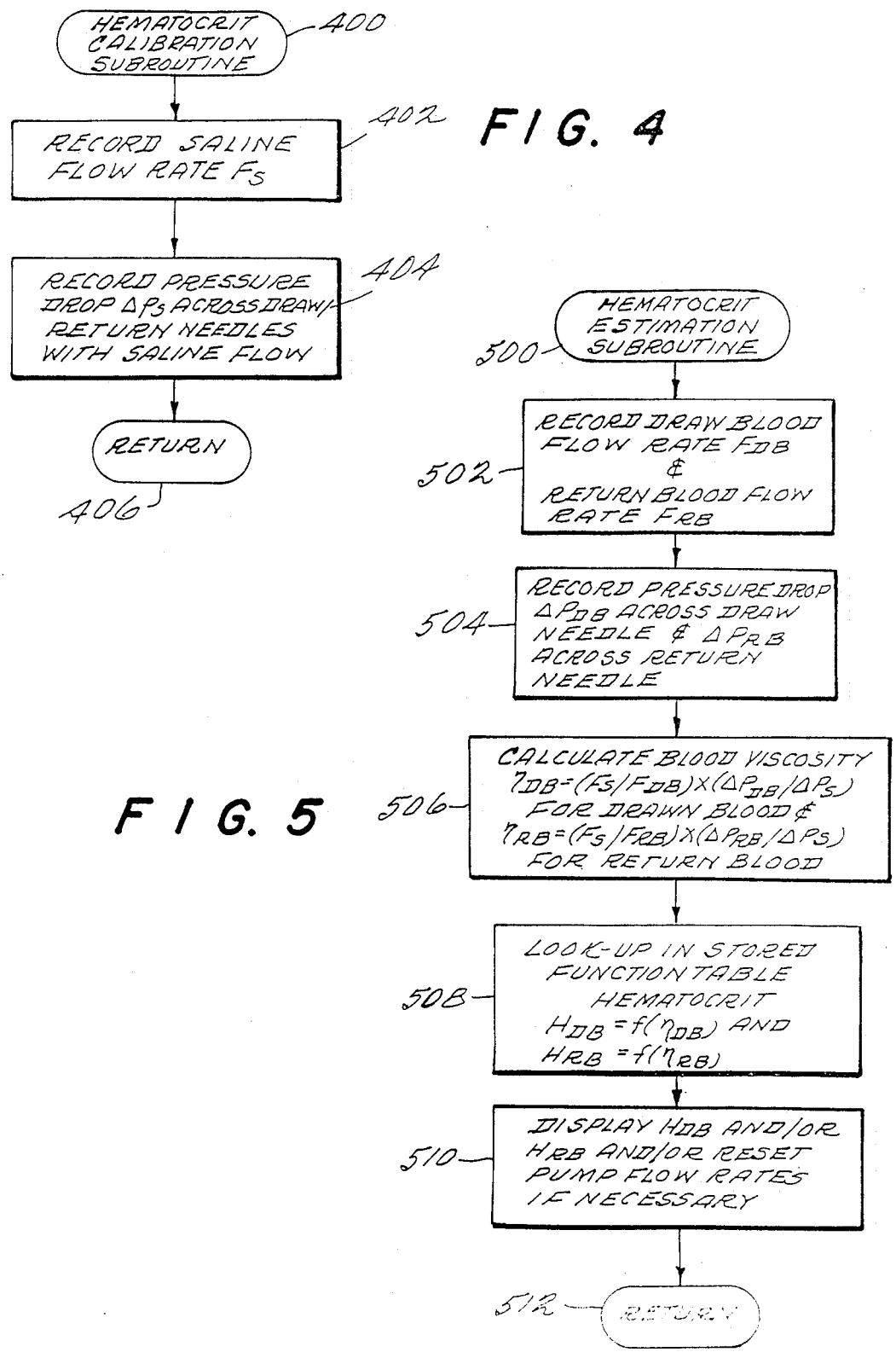

METHOD AND APPARATUS FOR ESTIMATING HEMATOCRIT IN A BLOOD CONSTITUENT PROCESSING SYSTEM

This is a continuation of application Ser. No. 06/920,341, filed Oct. 17, 1986, now abandoned.

This invention is generally directed to a fluid processing system where the fluid viscosity of a working fluid is measured by inference from pressure/flow measurements earlier made using a reference fluid of known viscosity. It is particularly useful in a blood constituent processing system where the hematocrit of blood constituent containing fluids may be critical to the successful or efficient operation of the system since there are known or derivable relationships between blood constituent viscosity and hematocrit.

Blood constituent processing systems may, for example, be of the type which pass blood through a constituent separating device so as to obtain concentrated blood plasma and/or platelet constituents while returning residual blood constituents to the donor or making them available for other uses. In these and/or other blood constituent processing systems, the hematocrit of the blood (an accepted measurement of the percentage content of red blood cells) can often be related to a critical system control parameter. For example, the optimum and/or maximum flow rate through a blood constituent separating device (so as to avoid hemolysis) may be directly related to the hematocrit of blood constituent containing fluid flows.

Unfortunately, hematocrit, even of whole blood directly from a human donor, may vary considerably from one donor to the next depending upon age, sex or other criteria. If an excessive flow rate occurs for the existing hematocrit, then unacceptable separation processes may result thus contaminating or otherwise making unusable the entire output of a given processing run. While there are known techniques for determining the hematocrit of a donor's blood, it may be undesirable and/or unacceptable for various reasons to prick a donor's finger or otherwise obtain an initial blood sample. In addition, the process necessarily consumes additional time and other facility resources and is subject to human operator mistakes.

Accordingly, in some blood constituent processing systems, an automatic iterative procedure has been adopted to empirically determine something close to an optimum blood flow rate. However, because of the criticality of the flow rate parameter, such procedures typically begin with an extremely conservative value and then only very slowly adapt towards an optimum value. For example, although one might typically expect to pump a platelet concentrate out of a separator device at approximately 6 millimeters per minute (assuming a typical blood flow input of 50 milliliters per minute), one might start out at a conservative rate (e.g. 3 milliliters per minute) equal to only half the typically expected final rate and then slowly increase the pumping rate of concentrate in small increments (e.g. over an adaptation period of perhaps 20 minutes out of a total processing session of 90 minutes per donor). It follows that if one could somehow accurately estimate the actual hematocrit, then one could much more quickly adjust to the optimum flow rates based upon known or easily derived relationships between hematocrit and optimum flow rates.

The rate at which residual blood constituents are returned to the patient may also be critically related to hematocrit of those residual constituents. While the optimum rate for returning packed red cell blood constituents to the patient are related to patient health and/or comfort, the critical input flow rates to the separator device are typically required so as to avoid undue hemolysis and/or to ensure proper blood constituent separation efficiency/efficacy.

I have now discovered method and apparatus for accurately estimating the hematocrit of blood constituents in such a blood constituent processing system. In brief, I have discovered method and apparatus for accurately estimating the viscosity of such blood constituent containing fluids and, once the viscosity is known, then using known relationships between blood viscosity and hematocrit for obtaining a hematocrit estimate. The technique may also have application in other fluid processing systems wherein a reference fluid of known viscosity and measurable pressure differentials may be utilized on a comparison basis with a working fluid so as to determine the unknown and possibly changing viscosity of the working fluid.

In existing blood processing systems (e.g. such as platelet separation systems), a known liquid such as saline solution is already utilized during a priming procedure which can be easily adapted so as to calibrate a flow restrictor within the fluid circuit and which can later be used as a transfer standard so as to measure (by inference) the viscosity of the working fluid (e.g. whole blood or other blood constituent containing fluids).

It is well known that the pressure drop across a known flow restrictor provides a linear measure (within flow limits) of fluid viscosity. However, the pressure drop across a small diameter flow restrictor (e.g. as in a blood draw/blood return needle orifice) varies as the fourth power of the restrictor diameter. This requires very precise control of the restrictor, or accurate calibration.

A typical blood constituent processing system includes a priming sequence wherein saline solution is pumped through all fluid flow paths so as to rid a disposable plastic tubing set of air prior to the introduction of blood to the system. During this initial priming procedure, a known flow rate of saline solution having a known viscosity may be caused to flow through at least one needle orifice which will later be used for blood flow. In the exemplary embodiment, separate blood draw and blood return needles are employed and they are temporarily housed within a common closed fluid container during the priming procedure with the saline solution being pumped serially through one of the needles, the common chamber, and the other needle. In the exemplary embodiment, to simplify matters and permit use of existing apparatus, it may be assumed that both needles in a given set are identical (i.e. that they have the same sized orifice and that they therefore have equal pressure drops).

Blood or blood constituent containing fluids will later flow through these same needles and for several reasons (some of which are already expressed above), the viscosity of the draw blood and the viscosity of the return blood are desirable parameters to determine and use for appropriate control purposes within the system (e.g. for controlling the flow rate of blood drawn from the donor's vein, for controlling the flow rate of packed blood cell fluid returning to a donor vein and/or for controlling the rate at which platelet, plasma or other blood constituent concentrates are extracted from a separation device.

Since the blood draw and blood return needles are also stable flow restrictors (i.e. the orifice diameter of a given needle will not materially change during blood flows), and since pressure sensors are already suitably positioned within the system and accommodated by existing disposable plastic tube sets, it is possible to obtain relative pressure drop and flow measurements using the saline solution of known viscosity during the priming procedure which data can, in turn, be utilized as relative calibration constants so as to determine the viscosity of blood or blood components later flowing through the same needles (and from which thus determined blood viscosity values and hematocrit values can be inferred from known relationships).

For example, suppose the pressure drop across the draw needle is 43 mmHg at a flow rate of 100 milliliters per minute of saline solution and further assume that the known relative viscosity of the saline solution is 1.0 at 20° C. Suppose that during subsequent blood constituent processing operations, the fluid pressure across the blood draw needle for whole blood is 76 mmHg. The relative viscosity of the whole blood is then simply equal to [flow rate saline/flow rate blood]×[pressure blood/pressure saline]=[100/50]×[76/43]=3.53. In effect, since the calibrating measurements for the needle were made at approximately 20° C. where the relative viscosity of water and saline solution is substantially 1.0 (except for possible needle temperature effects), the needle will automatically become a relative viscosity measuring instrument for blood at the usual blood temperature of about 37° C. (which typically is also the assumed blood temperature for blood viscosity measurements). Based on known relationships between blood viscosity and hematocrit (e.g. see FIG. 3) it can now be accurately estimated that since the blood relative viscosity has a value of 3.53, the hematocrit is approximately 55.

These as well as other objects, advantages and features of this invention will be more completely understood and appreciated by carefully reading the following detailed description of a presently preferred exemplary embodiment taken in conjunction with the accompanying drawings, of which:

FIG. 4 is a flow chart of a suitable hematocrit calibration subroutine which may be utilized by the microprocessor-based controller during an initial priming procedure of FIG. 1; and FIG. 5 is a flow chart of a hematocrit estimation subroutine which may be utilized by the microprocessor-based controller during subsequent blood constituent processing operations as depicted in FIG. 2.

Figure 1:
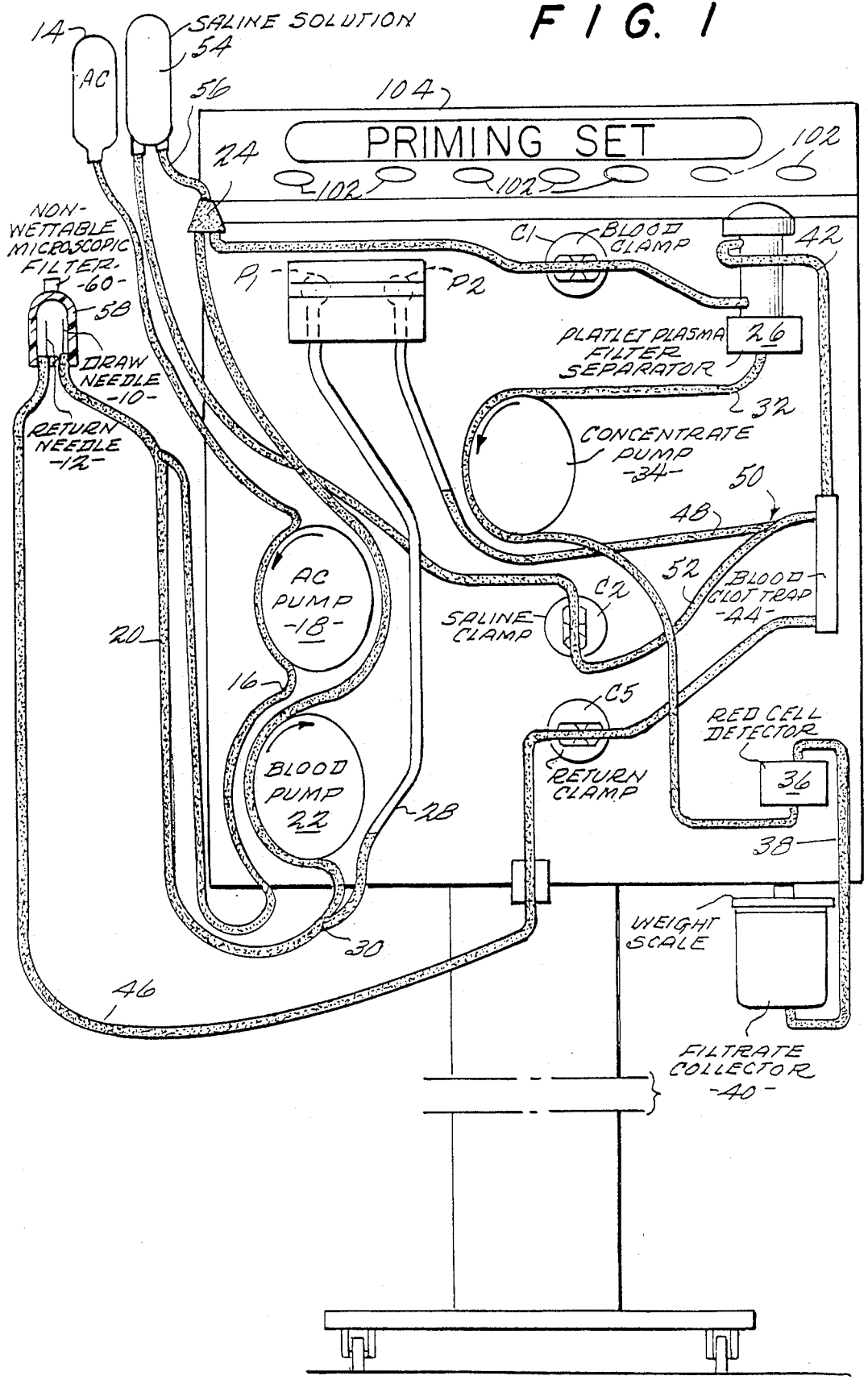
FIG. 1 depicts a blood constituent separating system in an initial priming procedure suitable for obtaining viscosity calibration data using a known saline solution.

A blood constituent processing system capable of separating platelets and/or plasma from a donor and returning the residual blood constituents to the donor is depicted in FIG. 1. In this particular exemplary system, two needles happen to be employed. A draw needle 10 is used to extract whole blood from a patient or donor and a return needle 12 is used to return residual/treated blood constituents to the donor (e.g. through a vein located in a different part of the body from the draw needle location). The entire fluid flow path including all interconnecting tubing, the platelet separator/plasma filter and the like are typically defined by a disposable plastic tubing harness or set which also includes the draw needle 10 and return needle 12. This disposable tubing set is then manually inserted into the apparatus of FIG. 1 so as to be mechanically coupled to various peristaltic pumps, pressure sensors, electromagnetically operated clamps, and the like. An anticoagulant is typically metered from supply 14 through line 16 by a controlled pump 18 into the drawn blood supply near the draw needle 10. Drawn blood is pumped through draw needle 10 and plastic tubing 20 in the direction of the arrow by a controlled peristaltic blood pump 22, through a filtering trap 24, an opened blood clamp C1 and to the input side of the platelet separator/plasma filter device 26. It will also be observed that a pressure transducer branch tubing 28 is connected to the draw line 20 near location 30 (and typically includes an upper volume of trapped air) communicating with the pressure transducer P1.

The filtrate from the separator/filter device 26 is pumped through line 32 by a controlled peristaltic concentrate pump 34 and on through a photosensitive red cell detector 36 and tubing 38 to a filtrate collector bag 40.

The residual blood constituents from separator/filter 26 pass out through line 42 through a blood clot trap 44, opened return clamp C5 and back to the return needle 12 via tubing 46. It will also be observed that the pressure of the return line may be monitored via branch line 48 connected at juncture 50 (and typically including a volume of trapped air) communicating with pressure transducer P2. A saline branch line 52 is also connected near junction 50 passing through electromagnetically controlled clamp C2 and back to the saline source 54 (which is also connectable via tubing 56 to the filter trap 24 and, therefore, to the draw side of the fluid circuit).

During conventional initial priming procedures, the system of FIG. 1 primes the fluid circuit with saline solution from supply 54. At some portion of the priming procedure, the draw needle 10 and return needle 12 will still be housed within their initially supplied antiseptic container 58 (which may include a nonwettable microscopic air filter 60 which, when disposed vertically, permits any included air to exit from the system but which does not permit the entry of microbes nor the exit of saline solution). During this portion of the priming procedure, the saline solution may be pumped (in either direction) by blood pump 22 around a fluid circuit in which the saline solution passes, inter alia through tubing 46 and return needle 12, the common fluid chamber 58, draw needle 10 and tubing 20. The rate of such flow may be controlled to a known or predetermined value by controlling the operation of blood pump 22 and the relative pressure across the orifices of the return and draw needles may also be monitored via pressure transducers P1 (at the low pressure side of the draw needle 10) and P2 (at the high pressure side of the return needle 12).

Although it would be preferable to know the exact pressure drop across each individual needle 10, 12, this might require measuring the relative pressure within container 58. To avoid such extra complexity, in the exemplary embodiment, it is merely assumed that the two needles within a given disposable set will have identical fluid flow characteristics. Accordingly, the pressure drop across the pair of serially connected needles P2—P1 is simply divided by two to obtain an assumed pressure drop across either one of the two needles. (Pressure transducers P1 and P2 may be initially calibrated to a common "base line" reading at zero flow conditions so as to reduce errors as will be appreciated).

Figure 2:
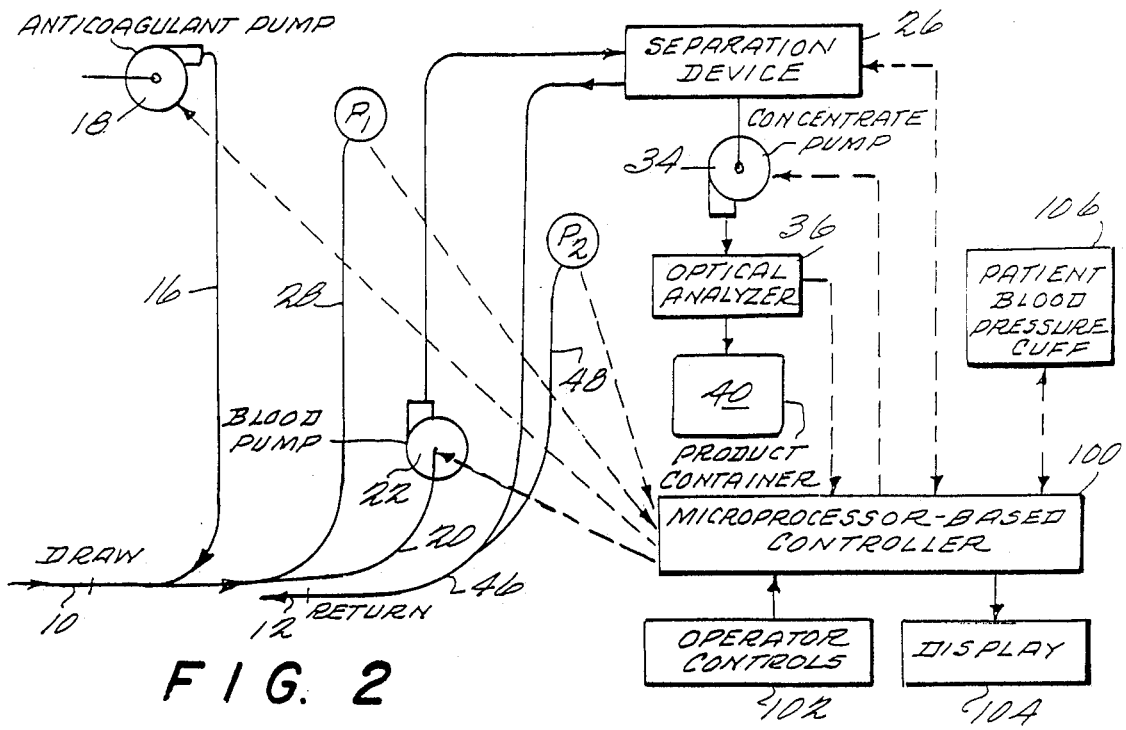
FIG. 2 is a schematic depiction of the FIG. 1 system illustrating a subsequent blood constituent processing operation and a microprocessor-based controller for controlling the various pumps, monitoring pressure transducers, and interfacing with a human operator.

The system of FIG. 1 is schematically depicted again in FIG. 2 where solid lines are used to indicate fluid flow connections and dotted lines are used to indicate electrical connections to the microprocessor-based controller 100. As will be understood, human operator interface with the microprocessor-based controller 100 may be achieved via operator control switches 102 and visual display 104. As depicted in FIG. 2, the draw and return needles 10, 12 now have been removed from their initial antiseptic container 58 and inserted within a patient so as to draw blood into the process and to return residual blood constituents to the donor. A conventional patient blood pressure measuring cuff 106 may also be employed so as to obtain a measure of the patient's blood pressure. Here, the viscosity calibration factors earlier determined using saline solution during the initial priming procedure may be utilized to accurately estimate hematocrit of the drawn and returned blood flows passing through needles 10, 12.

As presumably noted, the relationship between pressure drop, flow rate, viscosity and orifice diameter varies as the fourth power of the diameter:

$$F \alpha \frac{D^4 \Delta P}{\eta} \quad \text{[Equation 1]}$$

$$\eta \alpha (D^4 \Delta P)/F \quad \text{[Equation 2]}$$

where:
F = the fluid flow rate through a flow restricting orifice
D = the diameter of the flow restricting orifice
$\eta$ = the viscosity of the fluid
$\Delta P$ = the pressure drop across the orifice In the system of FIGS. 1 and 2 there are in reality two orifices of interest, each having its respective diameter: $D_{DB}$ (for the "draw blood" needle) and $D_{RB}$ (for the return blood needle). To simplify matters, for a given set of disposable needles, it is now assumed that $D = D_{DB} = D_{RB}$. Therefore, during the priming procedure, the saline solution pressure drop $\Delta P_{DBS}$ across the drawn blood ("DB") needle can also be assumed to equal the pressure drop $\Delta P_{RBS}$ across the return blood ("RB") needle. Thus, for the saline solution: $\Delta P_S = \Delta P_{DBS} = \Delta P_{RBS}$. During the priming procedure when the needles are connected in series, it is also known that the flow rates ($F_{DBS}$, $F_{RBS}$) of saline solution through the draw blood ("DB") and return blood ("RB") needles are also equal: $F_S = F_{DBS} = F_{RBS}$ and that flow rate $F_S$ is determined by the controlled blood flow pump 22.

During the priming procedure when saline solution fills the liquid flow paths, the combined pressure drop across both the DB and RB needles can be measured via P1 and P2:

$$2\Delta P_S = P2_S - P1_S \quad \text{[Equation 3]}$$

Therefore it follows that:

$$\eta_S \alpha (D^4 \Delta P_S)/F_S = [D^4 (P2_S - P1_S)/2]F_S \quad \text{[Equation 4]}$$

During actual blood flows, it also follows from Equation 2 that:

$$f_{DB} \alpha (D^4 \Delta P_{DB}) F_{DB} \quad \text{[Equation 5]}$$

$$f_{RB} \alpha (D^4 \Delta P_{RB})/F_{RB} \quad \text{[Equation 6]}$$

where
$\eta_{DB}$ = the viscosity of the drawn blood
$\Delta P_{DB}$ = the measured pressure drop across the drawn blood needle
$F_{DB}$ = the controlled flow rate of blood pump 22
$\eta_{RB}$ = the viscosity of the returned blood
$\Delta P_{RB}$ = the measured pressure drop across the return blood needle
$F_{RB}$ = the flow rate of return blood (i.e. $F_{DB}$—the flow rate of filtrate)

Then, by ratioing Equation 5/Equation 4 and Equation 6/Equation 4, one obtains:

$$\eta_{DB} = \eta_S (F_S/F_{DB}) \times (\Delta P_{DB}/\Delta P_S) \quad \text{[Equation 7]}$$

$$\eta_{RB} = \eta_S (F_S/F_{RB}) \times (\Delta P_{RB}/\Delta P_S) \quad \text{[Equation 8]}$$

And $\eta_S = 1.0$ in this example.

To measure the pressure drops $\Delta P_{DB}$ and $\Delta P_{RB}$, the system may be controlled to effect a zero DB and RB flow rate thus permitting P1 and P2 to provide a measure of the then existing venous pressure on the distal side of the DB and RB needles respectively. The pumps then may be rather quickly run up to a predetermined value (e.g. 50 ml/min) and another reading of P1 and P2 provides the relative fluid pressures on the near side of the needle orifices for that flow rate. The difference between the zero flow and non-zero flow pressure measurements then provide the $\Delta P_{DB}$ and $\Delta P_{RB}$ values.

Figure 3:
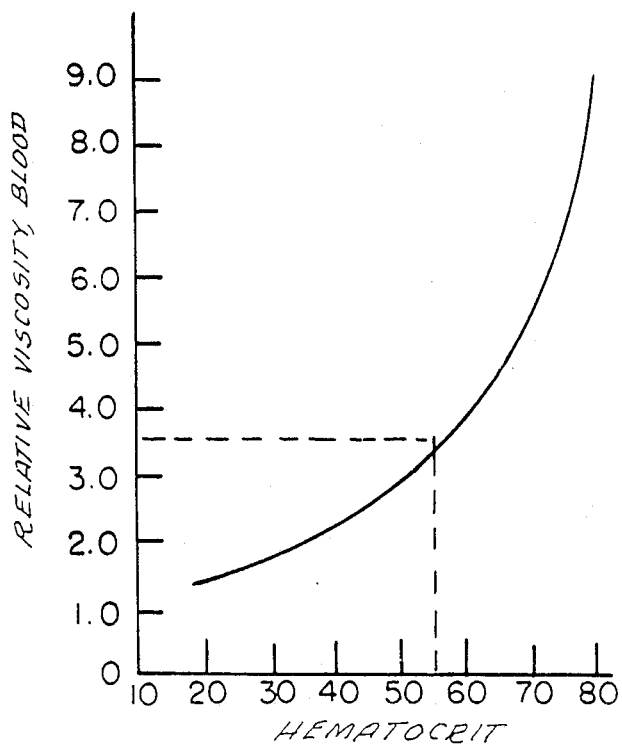
FIG. 3 is a graphical depiction of the known relationship between hematocrit and relative blood viscosity at an assumed temperature of 37° C.

Since all of the terms in Equations 7 and 8 are either determined during the initial calibration/priming procedure using the saline solution or are readily determinable at any point during a subsequent blood constituent processing operation, it follows that the viscosity of both the drawn and return blood can be readily calculated. Once such viscosity values are in hand, then there is a known relationship between hematocrit and absolute blood viscosity at 37° C. which is depicted in FIG. 3. Using the calculated blood viscosity values, a simple look-up table routine may be employed (e.g. in conjunction with a prestored table of values representing the curve shown in FIG. 3) so as to derive an accurate estimate for hematocrit. Alternatively, an analytic mathematical expression might be derived (e.g. to represent the curve shown in FIG. 3) and the hematocrit could then be analytically calculated using such a formula.

Although those in the art will be capable of devising many types of software and/or hardware modifications to a typical blood constituent processing system so as to practice the method of this invention, one suitable set of software subroutines which might be employed with the microprocessor controller of FIGS. 1 and 2 is depicted at FIGS. 4 and 5.

For example, during the initial priming procedure, and during a time when saline solution is flowing serially through the drawn blood and return blood needles 10, 12 and the interconnecting chamber 58, the hematocrit calibration subroutine 400 of FIG. 4 may be entered. Alternatively, these software modifications might be embedded directly in the portion of the software which controls the priming procedure. The calibration procedure can also be performed twice (once for fluid flow in one direction and then again for fluid flow in the other direction)—or even more—with the individual results being averaged. At step 402, the saline solution flow rate $F_S$ is recorded and at step 404, the pressure drop $\Delta P_S$ is recorded (i.e. one-half the combined pressure drop across both the draw and return needles as measured by transducers P1 and P2 in the exemplary embodiment). A normal exit or return to the regular priming program may be had at step 406.

Subsequently, during normal blood constituent processing, entry may be made (whenever desired) to the hematocrit estimation subroutine 500 of FIG. 5. Here, at step 502, a record is made of the then current draw blood needle flow rate $F_{DB}$ and of the return blood needle flow rate $F_{RB}$ (equal to the difference between the flow rates of the blood pump 22 and the concentrate pump 34). At step 504, a record is taken of the pressure drop $\Delta P_{DB}$ across the draw blood needle and $\Delta P_{RB}$ across the return blood needle. (As previously mentioned, this may involve a controlled zero flow period so as to obtain P1 and P2 data for the current venous pressure on the distal side of the needle orifices.) Thereafter, at step 506, the blood viscosities for both the drawn and return blood are calculated using the formulas of Equations 7 and 8. At step 508, the predetermined and known functional relationship between hematocrit and blood viscosity is utilized either in a conventional look-up table routine or via a suitable analytic formula to derive an accurate estimate for the drawn blood hematocrit $H_{DB}$ and for the return blood hematocrit $H_{RB}$. Finally, at step 510, the hematocrit estimates may be displayed (e.g. see display 104 in FIG. 1) and/or the pump flow rates may be reset as necessary to maintain optimum flow rates through the system for the current estimate of hematocrit. Return to regular system control software functions may be had at 512 as should be apparent.

While only one exemplary embodiment of the invention has been described in detail, those skilled in the art will recognize that many modifications and variations may be made in this exemplary embodiment while still retaining many of the novel features and advantages of this invention. Accordingly, all such modifications and variations are intended to be included within the scope of the appended claims.

What is claimed is:

1. A method for estimating the hematocrit of blood constituents in a blood constituent processing system, said method comprising the steps of:
   during an initial priming procedure of a blood constituent processing system when a fluid flow system including at least one blood flow needle is primed with a predetermined fluid of known viscosity, measuring the pressure drop across the orifice of said needle at a first flow rate using said fluid of known viscosity;
   during subsequent blood constituent processing operations of said system, measuring the pressure drop across said needle orifice for a second known flow rate of blood constituents;
   determining a blood viscosity value as a function of the measured pressure drops and flow rates; and
   determining a hematocrit value for said blood constituents as a function of said blood viscosity value.

2. A method as in claim 1 wherein said predetermined fluid is a saline solution having a viscosity of approximately 1.0 at 20° C.

3. A method as in claim 1 wherein said blood constituent processing system includes both a blood draw needle and a blood return needle which, during the priming procedure, are commonly disposed within a fluid containing chamber with said predetermined fluid being pumped serially through said needles and chamber, each needle being assumed to have an approximately equal pressure drop thereacross which is equal to one-half the actually measured fluid pressure drop appearing across the fluid-connected series combination of the needles and chamber.

4. A method as in claim 3 wherein during said subsequent blood constituent processing operations:
   the pressure drop across the draw needle and across the return needle are both measured for respectively associated known draw and return flow rates;
   a first blood viscosity value is determined for drawn blood and a second blood viscosity value is determined for returned blood; and
   a first hematocrit value is determined for drawn blood and a second hematocrit value is determined for returned blood.

5. Apparatus for estimating the hematocrit of blood constituents in a blood constituent processing system, said system comprising:
   means for performing an initial priming procedure within a fluid flow system including at least one blood flow needle primed with a predetermined fluid of known viscosity;
   means for measuring the pressure drop across the orifice of said needle at a first flow rate using said fluid of known viscosity;
   means for performing subsequent blood constituent processing operations;
   means for measuring the pressure drops across said needle orifice for a second known flow rate of blood constituents;
   means for determining a blood viscosity value as a function of the measured pressure drops and flow rates; and
   means for determining a hematocrit value for said blood constituents as a function of said blood viscosity value.

6. Apparatus as in claim 5 using a saline solution having a viscosity of approximately 1.0 at 20° C. as said predetermined fluid.

7. Apparatus as in claim 5 wherein said blood constituent processing system includes both a blood draw needle and a blood return needle which, during the priming procedure, are commonly disposed within a fluid containing chamber with said predetermined fluid being pumped serially through said needles and chamber, each needle having an approximately equal pressure drop thereacross which is equal to one-half the actually measured fluid pressure drop appearing across the fluid-connected series combination of the needles and chamber.

8. Apparatus as in claim 7 including means operative during said subsequent blood constituent processing operations to:
   measure the pressure drop across the draw needle and across the return needle for respectively associated known draw and return flow rates;
   determine a first blood viscosity value for drawn blood and a second blood viscosity value for returned blood; and
   determine a first hematocrit value for drawn blood and a second hematocrit value for returned blood.

* * * * *